United States Patent [19]

Helenowski

[11] Patent Number: 4,548,516
[45] Date of Patent: Oct. 22, 1985

[54] SEQUENTIAL THERMOGRAPHY FLUID FLOW INDICATOR

[76] Inventor: Tomasz K. Helenowski, 6831 N. Algonquin Ave., Chicago, Ill. 60646

[21] Appl. No.: 686,094

[22] Filed: Dec. 24, 1984

[51] Int. Cl.[4] .............................................. G01F 1/68
[52] U.S. Cl. .................................... 374/135; 374/147; 128/691; 604/9; 73/204
[58] Field of Search ............... 374/135, 138, 147, 148; 128/691, 692, 736; 604/8, 9; 73/204

[56] References Cited

U.S. PATENT DOCUMENTS

| | | | |
|---|---|---|---|
| 1,758,532 | 5/1930 | Phinney | 374/148 |
| 2,627,182 | 2/1953 | Quereau | 374/135 |
| 3,288,142 | 11/1966 | Hakim | 604/9 |
| 3,345,874 | 10/1967 | Carnoil et al. | 374/135 |
| 3,452,757 | 7/1969 | Ames | 604/8 |
| 3,623,473 | 11/1971 | Andersen | 128/691 |
| 3,874,239 | 4/1975 | Finney | 374/147 |
| 4,354,504 | 10/1982 | Bro | 128/691 |

FOREIGN PATENT DOCUMENTS 2034480  6/1980  United Kingdom ............... 374/138

Primary Examiner—Charles Frankfort
Assistant Examiner—Thomas B. Will

[57] ABSTRACT

An apparatus for indicating the fluid flow through implanted shunts by temperature sensing. The sensor comprises a series of thermistors carried by a flexible substrate mounted on a rigid support. The sensors are placed in external proximity to a section of the implanted shunt and by varying the temperature of the fluid proceeding the test section, the apparatus will determine the rate of flow therethrough. Each thermistor is connected by conductors to scaling and amplification circuitry for input into a computer system.

10 Claims, 4 Drawing Figures

SEQUENTIAL THERMOGRAPHY FLUID FLOW INDICATOR

SUMMARY OF THE INVENTION

The present invention relates to an apparatus and method of sensing the fluid flow in implanted shunt paasages such as are used in the drainage of fluids from one part of the body to another. The sequential thermography fluid flow indicator is employed to determine the condition of the implanted shunts by establishing the temperature of the fluid flow therein, so as to avoid unnecessary surgery or certainly to be able to determine with specificity partial or complete clogging of the shunt.

More specifically it has been found that the treatment of hydrocephalus, a disease in which extra fluid is present in the brain, requires drainage of this fluid from the brain to another part of the body where it can be absorbed. This is normally accomplished by placing a flexible tube recognized as a shunt between the fluid filled cavity to another portion of the body, usually the abdominal cavity. While this accepted practice of shunting is recognized in the medical profession the continuing and existing problem of clogging of the shunts has persisted. The methods presently available for determining shunt function are frequently in error. These errors may lead to unnecessary hospitalizations and, in come cases, to unnecessary surgery. The present invention determines the condition of the shunts.

By employing my device, which computerizes the sensed temperature and rate of fluid flow, surgery is eliminated in these cases. I provide a device which by selected temperature probes will first indicate a temperature reference of the body skin, and then, by a series of additional temperature probes or thermistors, the temperature of the body skin adjacent to a predetermined length of shunt through which the drainage flows can be determined. This information can be amplified and displaced and or registered into a computer program.

With the shunt in place the apparatus of my invention will determine the temperature of the environs of the shunt, as well as the skin temperature adjacent to such shunt. The fluid in the shunt upstream of the apparatus has its temperature reduced in a manner such as placing ice upon the external skin area of the shunt. As the cooled fluid flows through the shunt the resulting temperature variances are sensed and such information will be used to determine the rate of flow within the tested shunt area.

Other objects of the invention will be hereinafter made apparent from a reading of the detailed description of the apparatus and its method of operation.

BRIEF DESCRIPTION OF THE DRAWINGS

The invention will be best understood by reference to the accompanying drawings showing the preferred construction and mode of operation of the invention by which the stated objects thereof are achieved and in which.

GENERAL DESCRIPTION

Figure 1:
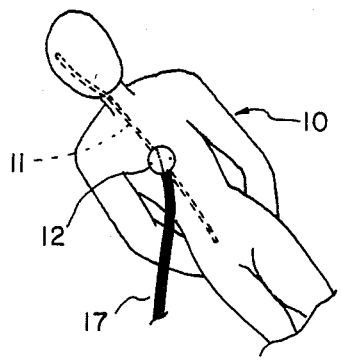
FIG. 1 is a perspective fragmentary view of the Sequential Thermography Fluid Flow Indicator in an operative position.

Referring to FIG. 1 there is illustrated a physical body 10 having outlined in dotted lines a shunt 11 which normally comprises a plastic tubing or the like. These shunts were primarily employed to drain excess fluid build up into other body cavities where such excess fluid could be readily absorbed.

In FIG. 1, the Sequential Thermography Fluid Flow Indicator, provides a probe 12, shown in place on the external surface of the skin in close proximity to the shunt 11.

Figure 2:
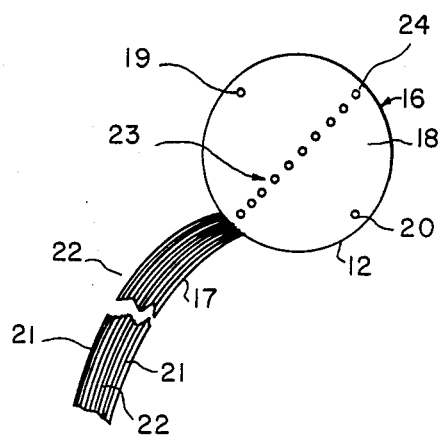
FIG. 2 is a top plane fragmentary view of the invention.
Figure 3:
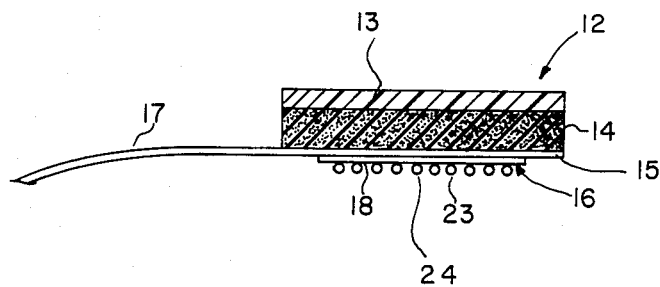
FIG. 3 is a fragmentary detailed side elevational view of the invention.
Figure 4:
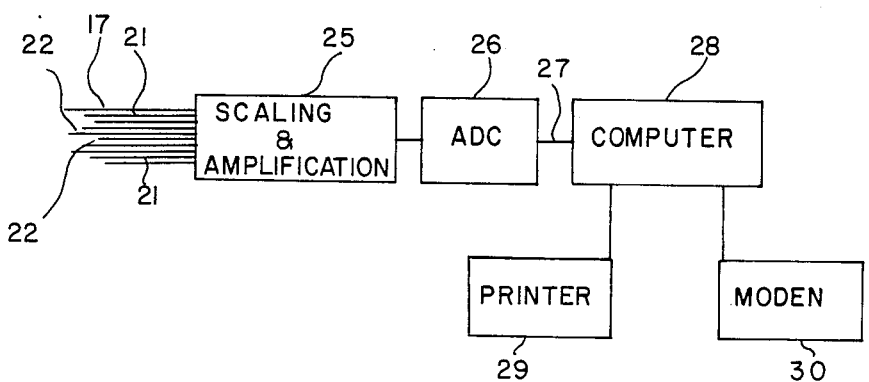
FIG. 4 is a block diagram of the computerized sequential thermography equipment associated with the invention.

As more clearly shown in FIGS. 2 and 3 the probe 12 comprises a base support 13 formed from a rigid material which has, adhesively attached to one surface thereof, an element of flexible material 14 such as a sponge or the like. Beneath the exposed surface of the flexible material 14 is a flexible plastic disc, circuit board 15, one facial surface of which is covered by a disc-like shaped cable head 16 of a ribbon cable 17. On the exposed surface of the cable head 16 are a plurality of thermistor ends.

Referring to FIG. 2 it is seen that the cable head 16 on its exposed face 18 displays the sensor tips 19 and 20 of certain conductors 21 which form part of the ribbon cable 17. There is also exposed a linear series 23 of sensor tips 24 having conductors 22 that also form part of the ribbon cable 17.

In operation the linear series 23 of the sensor tips 24 are caused to lie in alignment with the section of the implanted shunt 11 to be tested.

The sensor tips 19 and 20 are reference thermistors for scaling the system for a base skin temperature. The linear series 23 of the sensor tips 24 will progressively sense the temperature change in the fluids passing through the shunt 11.

When the probe 12 has been placed upon the skin in proximity to the shunt 11 the temperature of the surrounding skin is determined by the sensor tips 19 and 20. An ice pack or some other form of coolant is placed on the upstream side of the shunt 11. The fluid in the shunt 11 is cooled and as it flows down the tubing the skin temperature adjacent thereto is cooled and this change in temperature is in turn sensed by the sensor tips 24 in the linear series 23. By the data obtained the rate of fluid flow in the shunt 11 can be determined.

As shown in the block diagram of FIG. 3 the probe 12 through its ribbon cable may be placed in circuit with a temperature reference or scaling and amplification unit 25. This information is fed into an Analogue to Digital converter 26 which in turn by interface 27 is connected to a computer 28. The computer may in turn be connected to a printer 29 for making a permanent record or may be interfaced to a modem 30 for connecting the same to a central data bank.

While I have illustrated and described the preferred form of construction and method for carrying out the invention this is capable of variation and modification without departing from the spirit of the invention. I therefore do not wish to be limited to the various details but desire to avail myself of such variations and modifications as come within the scope of the appended claims.

Having thus described my invention what I claim as new and desire to protect by Letters Patent is:

1. An apparatus for non-invasively determining the rate of flow of fluids in an embedded shunt through thermal comparisons comprising,
    (a) a probe having a rigid base layer, an intermediate layer of resilient material and a flexible circuit board,
    (b) an aligned series of temperature sensing elements carried by the exposed surface of said circuit board and adapted to be placed in linear alignment with the embedded shunt for progressively sensing a temperature change in the fluid as its flows through the shunt,
    (c) a pair of temperature sensitive elements carried by said circuit board to either side of said aligned series of temperature sensitive elements for sensing the temperature of an adjacent area of the embedded shunt so as to establish a reference temperature source,
    (d) conduit means connecting all of said temperature sensing elements to an information gathering and analysis source, and
    (e) said information gathering and analysis source registering and indicating the progressive change in temperature of the fluid as it flows through the embedded shunt and for calculating the rate of flow by said progressive temperature variances.

2. An apparatus for non-invasively determining the rate of flow of fluids in an embedded shunt as defined by claim 1 wherein said series of temperature sensing elements and said pair of temperature sensing elements are thermistors having exposed thermal conductive heads.

3. An apparatus for non-invasively determining the rate of flow of fluids in an embedded shunt as defined by claim 1 wherein said conduit means is a ribbon cable consisting of individual conductive lines, one for each temperature sensitive element.

4. An apparatus for non-invasively determining the rate of flow of fluids in an embedded shunt as defined by claim 1 wherein said conduit means is a ribbon cable consisting of individual conductive lines, one for each thermistor.

5. An apparatus for non-invasively determining the rate of flow of fluids in an embedded shunt as defined by claim 1 wherein said information gathering and analysis source includes a computer adapted to analyze the sensed temperature changes in the fluid in the shunt as it flows beneath the aligned temperature sensing elements and to calculate the rate of flow of such fluids in the shunt.

6. An apparatus for non-invasively determining the rate of flow of fluids in an embedded shunt as defined by claim 5 wherein said series of temperature sensing elements and said pair of temperature sensing elements are thermistors having exposed thermal conductive heads.

7. An apparatus for non-invasively determining the rate of flow of fluids in an embedded shunt as defined by claim 5 wherein said conduit means is a ribbon cable consisting of individual conductive lines, one for each temperature sensitive element.

8. An apparatus for non-invasively determining the rate of flow of fluids in an embedded shunt as defined by claim 4 wherein said information gathering and analysis source includes a computer adapted to analyze the sensed temperature changes in the fluid in the shunt as it flows beneath the aligned thermistors and to calculate the rate of flow of such fluids in the shunt.

9. A method for non-invasively determining the rate of flow of fluids in an embedded shunt by thermal comparison comprising sensing the temperature of a mass adjacent to the embedded shunt for determining a base temperature reference, sensing the temperature of the fluid in the shunt and comparing such sensed temperature to the base temperature reference, reducing the temperature of the shunt as well as the fluid therein at a point preceeding it's temperature sensing, and subsequently progressively sensing the changed temperature of the fluid flowing in the shunt and analyzing the progressively changing temperatures of the fluid as it flows through the shunt for determining its rate of flow.

10. A method for non-invasively determining the rate of flow of fluids in an embedded shunt by thermal comparison as defined by claim 9 wherein the temperature sensors are thermistors.

* * * * *